United States Patent [19] [11] 3,954,854
Gehrmann et al. [45] May 4, 1976

[54] RECOVERY OF MONOMERIC ACRYLIC ACID FROM RESIDUES ORIGINATING FROM PROCESSED CRUDE ACRYLIC ACID

[75] Inventors: Klaus Gehrmann, Erfstadt Lechenich; Heinz Erpenbach, Surth near Cologne; Georg Kohl, Hurth-Burbach; Hans Klaus Kübbeler, Surth near Cologne, all of Germany

[73] Assignee: Hoechst Aktiengesellschaft, Frankfurt am Main, Germany

[22] Filed: Feb. 12, 1975

[21] Appl. No.: 549,176

[30] Foreign Application Priority Data
Feb. 15, 1974 Germany............................ 2407236

[52] U.S. Cl............................................. 260/526 N
[51] Int. Cl.² ........................................ C07C 51/00
[58] Field of Search ............................... 260/526 N

[56] References Cited
UNITED STATES PATENTS
2,485,510  10/1949  Redmon.......................... 260/526 N
3,086,046  4/1963  Kutepow et al................. 260/526 N
3,639,466  2/1972  Leichte........................... 260/526 N Primary Examiner—Vivian Garner
Attorney, Agent, or Firm—Connolly and Hutz

[57] ABSTRACT

Monomeric acrylic acid is recovered from residues originating from processed crude acrylic acid and containing β-acryloyloxypropionic acid, β-acetoxypropionic acid, hydracrylic acid, dihydracrylic acid and polymeric hydracrylic acid. To this end, the residues are heated to temperatures within the range 130° and 250°C under pressures within the range 0.01 and 1 atmosphere absolute in contact with catalysts selected from alkali metal or alkaline earth metal carboxylates, phosphates or borates, or from alkali metal or alkaline earth metal compounds producing carboxylates together with the carboxylic acids being contained in the residues.

4 Claims, No Drawings

RECOVERY OF MONOMERIC ACRYLIC ACID FROM RESIDUES ORIGINATING FROM PROCESSED CRUDE ACRYLIC ACID

It is known that crude acrylic acid can be processed, e.g. by a standard process comprising carboxylating acetylene with CO and water, or by a modern process comprising oxidizing propylene in contact with oxidic catalysts, with the resultant formation of residues consisting substantially of β-acryloyloxypropionic acid, β-acetoxypropionic acid, hydracrylic acid, dihydracrylic acid and polymeric hydracrylic acid.

It is accordingly the object of the present invention to recover acrylic acid from those residues.

Various processes for making monomeric acrylic acid from the above compounds have already been described in literature. U.S. Pat. No. 2,806,878, for example, describes a process wherein β-acryloyloxypropionic acid is resplit, at temperatures within the range 35° and 85°C under pressures within the range 10 and 100 mm of mercury, in contact with Friedel Crafts-catalysts, such as sulfuric acid, phosphoric acid, benzenesulfonic acid, p-toluenesulfonic acid, potassium bisulfate or $AlCl_3$. As taught in U.S. Pat. No. 2,469,701, hydracrylic acid is dehydrated at temperatures within the range 130° and 190°C under pressure lower than 100 mm of mercury in contact with acid dehydration catalysts, such as sulfuric acid, preferably in the presence of powdered copper, and acrylic acid is thereby recovered therefrom. German Pat. No. 1,151,501 describes a noncatalytic process for recovering acrylic acid from distillation residues, which substantially consist of diacrylic acid, hydracrylic acid, polyacrylic acid and monomeric acrylic acid, wherein the residues are vaporized under reduced pressure and caused to travel through containers maintained at temperatures within the range 350° and 650°C. German Pat. No. 1,189,986 describes a process, wherein acrylic acid residues are split in contact with acid catalysts at temperatures of at least 150°C with the addition of ethers or ether-forming alcohols which act as stabilizing solvents. A still further process for recovering monomer acrylic acid from the above distillation residues has been disclosed in German patent specification "Offenlegungsschrift" No. 1,618,129, wherein compounds having secondary or tertiary amino groups and tertiary phosphines are used as the catalysts.

As reported in German patent specification "Offenlegungsschrift" No. 1,618,129, the processes described in the above two U.S. Patents are not fully satisfactory in requiring long contact times during which the residues become very viscous and, in the end, hard. As a result, it is necessary for the reactors to be cleaned, which is very expensive. These two latter processes are further handicapped by the use of acids of high corrosiveness. Still further, the catalysts are very rapidly rendered resinous and inactive. In the process reported in German Pat. No. 1,151,501, the residues are very difficult to vaporize completely. The process described in German Pat. No. 1,189,986 uses concentrated sulfuric acid at high temperatures, which means strong corrosiveness. In addition to this, all of these earlier processes produce unsatisfactory yields of monomeric acrylic acid.

While the process disclosed in German patent "Offenlegungsschrift" No. 1,618,219 partially avoids the handicaps reported above, the fact remains that costly catalysts are used therein, which do not add to the economy of the process.

The present invention now provides a process for recovering monomeric acrylic acid from residues originating from processed crude acrylic acid and containing β-acryloyloxypropionic acid, β-acetoxypropionic acid, hydracrylic acid, dihydracrylic acid and polymeric hydracrylic acid, wherein the residues are cracked thermally under reduced pressure in the presence of catalysts, and the resulting monomeric acrylic acid is distilled off, which process comprises heating the residues to temperatures within the range 130° and 250°C under pressures within the range 0.01 and 1 atmosphere absolute in contact with catalysts selected from alkali metal or alkaline earth metal carboxylates, phosphates or borates, or from alkali metal or alkaline earth metal compounds producing carboxylates together with the carboxylic acids being contained in the residues.

The compounds producing carboxylates together with the carboxylic acids contained in the residues should more preferably be selected from carbonates, hydrogen carbonates, hydroxides, oxides or cyanides of alkali metals or alkaline earth metals. The preferred alkali metal or alkaline earth metal carboxylates include those which have from 1 to 4 carbon atoms. The catalyst should conveniently be used in proportions within the range 0.1 and 5 weight %, based on the weight of residue.

The process of the present invention provides for the selection of optimum catalysts from a wide variety of compounds for the recovery of monomeric acrylic acid in high yields from distillation residues, and avoids the adverse effects encountered in the above known processes.

In industry, it is good practice for the distillation residues to be cracked continuously and for the resulting monomeric crude acrylic acid to be delivered to the acrylic acid processing stage.

EXAMPLES 1 – 12

350 g of residue having the composition indicated hereinabove and obtained in the processing of acrylic acid was admixed with a cleavage catalyst and heated under pressure within the range 10 and 760 mm of Hg to the temperatures specified hereinafter, in a reactor having a capacity of 500 cc. A further 450 g of residue was added as the reaction went on. The residue used in the present Examples had an ester number of 340 (cf. F. Ullmann, Encyklopadie der technischen Chemie, 3rd edition, vol. VII (1956) 544. It was not necessary for a stabilizer, such as hydroquinone, to be added to the distillation residue which contained sufficient stabilizer originating from the work-up. 1 weight % of cleavage catalyst, based on the distillation residue, was used in each of Examples 2 to 12. The crude acrylic acid, which was distilled off, was collected in an intermediate receptacle and recycled to the acrylic acid processing stage. The crude acrylic acid contained 95 to 97.5 weight % of acrylic acid. The balance consisted substantially of acetic acid, dimeric acrylic acid and water.

Example 1 is given for the purpose of comparison.

TABLE

| Ex. | Catalyst | Pressure (mm Hg) | Temperature (°C) | Reaction period (h) | Crude acrylic acid (g) |
|---|---|---|---|---|---|
| 1 | — | 100 | 185 | 5 | 620 |
| 2 | Sodium acetate | 10 | 149 | 1.2 | 712 |
| 3 | Sodium acetate | 100 | 172 | 1.2 | 710 |
| 4 | Sodium acetate | 760 | 215 | 1.3 | 705 |
| 5 | Sodium acrylate | 100 | 171 | 1.15 | 714 |
| 6 | Potassium acetate | 100 | 172 | 1.1 | 725 |
| 7 | Calcium acetate | 100 | 178 | 2.1 | 664 |
| 8 | Barium acetate | 100 | 177 | 2.3 | 670 |
| 9 | Sodium carbonate | 100 | 172 | 1.2 | 715 |
| 10 | Sodium phosphate | 100 | 175 | 1.9 | 712 |
| 11 | Calcium phosphate | 100 | 176 | 2.5 | 680 |
| 12 | Sodium metaborate | 100 | 172 | 0.9 | 695 |

We claim:

1. A process for recovering monomeric acrylic acid from residues originating from processed crude acrylic acid and containing β-acryloyloxypropionic acid, β-acetoxypropionic acid, hydracrylic acid, dihydracrylic acid and polymeric hydracrylic acid, wherein the residues are thermally cracked by heating to temperatures within the range 130° and 250°C under pressures within the range 0.01 and 1 atmosphere absolute in contact with catalysts selected from alkali metal or alkaline earth metal carboxylates, phosphates or borates, or from alkali metal or alkaline earth metal compounds producing carboxylates together with the carboxylic acids contained in the residues, and the resulting monomeric acrylic acid so split off is distilled off.

2. A process as claimed in claim 1, wherein the compounds forming carboxylates with the carboxylic acids contained in the residues are selected from carbonates, hydrogen carbonates, hydroxides, oxides or cyanides of alkali metals or alkaline earth metals.

3. A process as claimed in claim 1, wherein the catalysts are alkali metal or alkaline earth metal carboxylates having from 1 to 4 carbon atoms.

4. A process as claimed in claim 1, wherein the catalyst is used in proportions within the range 0.1 and 5 weight %, based on the weight of residue.

* * * * *